(12) United States Patent
Shin et al.

(10) Patent No.: US 7,646,478 B2
(45) Date of Patent: Jan. 12, 2010

(54) APPARATUS AND METHOD FOR EXAMINING SPECTRAL CHARACTERISTICS OF TRANSMITTED LIGHT THROUGH AN OBJECT

(75) Inventors: Koung-Su Shin, Hwaseong-si (KR); Dong-Su Ha, Yongin-si (KR); Chung-Sam Jun, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 302 days.

(21) Appl. No.: 11/703,095

(22) Filed: Feb. 7, 2007

(65) Prior Publication Data

US 2007/0188748 A1 Aug. 16, 2007

(30) Foreign Application Priority Data

Feb. 10, 2006 (KR) ...................... 10-2006-0013083

(51) Int. Cl.
*G01N 21/00* (2006.01)
(52) U.S. Cl. .................. 356/237.5; 356/237.6; 356/432
(58) Field of Classification Search ................. 356/432, 356/237.1–237.5
See application file for complete search history.

(56) References Cited

U.S. PATENT DOCUMENTS

| | | | | |
|---|---|---|---|---|
| 5,262,891 A | * | 11/1993 | Nakasato | 359/385 |
| 6,775,000 B2 | * | 8/2004 | Harrison et al. | 356/432 |
| 7,355,692 B2 | * | 4/2008 | Noy et al. | 356/237.5 |
| 2004/0027556 A1 | * | 2/2004 | Baer et al. | 356/36 |
| 2004/0263960 A1 | * | 12/2004 | Obuchi | 359/385 |

FOREIGN PATENT DOCUMENTS

| | | |
|---|---|---|
| EP | 0 527 645 A1 | 2/1993 |
| JP | 05-062045 | 8/1993 |
| JP | 05-047907 | 2/1998 |
| JP | 10-170339 | 6/1998 |
| JP | 2002-310955 | 10/2002 |
| KR | 20-0150091 | 4/1999 |
| KR | 10-2005-0095063 | 9/2005 |

* cited by examiner

*Primary Examiner*—Gregory J Toatley, Jr.
*Assistant Examiner*—Rebecca C Slomski
(74) *Attorney, Agent, or Firm*—Lee & Morse, P.C.

(57) ABSTRACT

An apparatus for examining spectral characteristics of an object may include a chuck configured to support and releasably fix the object, wherein the chuck is larger than the object, a first light source assembly integral with the chuck and configured to illuminate a bottom surface of the object with light having a predetermined spectrum and intensity, and a transmission analysis unit for collecting and analyzing light transmitted through the object. The first light source assembly may include multiple and/or adjustable light sources. A second light source assembly may illuminate a top surface of the object, and a reflection analysis unit may collect resultant reflected light.

19 Claims, 3 Drawing Sheets

APPARATUS AND METHOD FOR EXAMINING SPECTRAL CHARACTERISTICS OF TRANSMITTED LIGHT THROUGH AN OBJECT

BACKGROUND OF THE INVENTION

1. Field of the Invention

The present invention relates to an apparatus and a method for examining spectral characteristics of an object. More particularly, the present invention relates to an automated apparatus and method for examining spectral characteristics of a color filter used in optical devices, liquid crystal display (LCD) panels and the like.

2. Description of the Related Art

Recently, there has been an increased demand for color filters with excellent qualities due to the rapid development of semiconductor and optical devices. The color filters may be formed by dying color registers or spraying pigments onto the color registers. The pigments must be carefully monitored during production in order for the color filters to be able to extract precise colors from an incident light source.

In a conventional production line for a 200 mm color filter, spectral characteristics of the 200 mm color filter may be detected and examined by a spectral module attached to a microscope. However, these systems have numerous shortcomings, including: the inability to examine a sample larger than a 200 mm substrate and the inability to accept substrates having a range of sizes. Further, even if the conventional apparatus could accept a 300 mm substrate for examination, the 300 mm substrate may be warped when mounted on the smaller chuck, and spectral characteristics of the 300 mm substrate may be distorted. In addition, the conventional apparatus requires that the substrate be loaded and unloaded manually. This sample replacement, whether manual or automatic, may expose a substrate to contaminates or damage the substrate.

SUMMARY OF THE INVENTION

The present invention is therefore directed to an apparatus for examining spectral characteristics of an object, which substantially overcomes one or more of the problems due to the limitations and disadvantages of the related art.

It is therefore a feature of an embodiment of the present invention to provide a method for examining spectral characteristics of an object regardless of size.

It is therefore a feature of an embodiment of the present invention to provide a method for automatically examining spectral characteristics of an object.

It is therefore another feature of an embodiment of the present invention to provide an environmentally-controlled apparatus that significantly reduces the possibility of the object becoming contaminated.

At least one of the above and other features and advantages of the present invention may be realized by providing an apparatus that includes a chuck configured to support and releasably fix the object, wherein the chuck is larger than the object, a first light source assembly integral with the chuck and configured to illuminate a bottom surface of the object with light having a predetermined spectrum and intensity, and a transmission analysis unit for collecting and analyzing light transmitted through the object.

The first light source assembly may include a plurality of light sources that are spaced apart from one another from a center of the chuck toward an outside of the chuck. The first light source assembly may include a plurality of light sources and light source driving members. The plurality of light sources may be arranged along a straight line. The first light source assembly may include a first light source formed at the center of the chuck, a second light source formed within a radius of about 100 mm from the center of the chuck, and a third light source formed within a radius of about 100 mm to about 150 mm from the center of the chuck.

The apparatus may include a second light source assembly oriented over the chuck to illuminate a top surface of the object, and a reflection analysis unit for collecting reflected light and for analyzing light reflected by the object.

The apparatus may further include a chuck driving member below the chuck to move the chuck horizontally. The chuck may include a chuck plate having a plurality of vacuum slits formed along a plurality of concentric circles in the chuck plate, wherein the vacuum slits do not overlay the first light source assembly, and a vacuum unit in communication with the vacuum slits to draw in air through the vacuum slits to releasably fix the object onto the chuck plate. The chuck plate may include a horizontal area that is substantially the same as or greater than that of the object. The chuck plate may include a first vacuum slit formed within a radius of about 100 mm from a center of the chuck plate, and a second vacuum slit formed within a radius of about 100 to about 150 mm from the center of the chuck plate.

The apparatus may further include a first light source formed at the center of the chuck plate, a second light source formed at substantially the same distance from the center of the chuck plate as the first vacuum slit, and a third light source formed at substantially the same distance from the center of the chuck plate as the second vacuum slit. The chuck plate may include a light slit extending radially from the center of the chuck plate toward an outside of the chuck plate, and the first light source may include a light source formed within the light slit, and a light source driving member for translating the light source along the light slit. At least one of the plurality of light sources may be capable of being moved radially from the center of the chuck.

The apparatus may further include a slider mechanism configured to support standard samples, and a slider driving member configured to move the slider inside the transmission analysis unit. The apparatus may further include a plurality of standard samples. The apparatus may further include an interface for receiving a loading unit for automatically loading the object onto the chuck.

The apparatus may further include a housing configured to contain the chuck, the first light source assembly and the transmission analysis unit to protect the chuck, the first light source assembly, and the transmission analysis unit from contaminants.

At least one of the above and other features and advantages of the present invention may be realized by providing a method for examining the spectral characteristics of an object, including mounting the object onto a chuck having a size larger than that of the object, illuminating a bottom surface of the object from a light source assembly integral with the chuck, collecting light transmitted by the object, and deriving a light transmission value for the object. A light reflection value for the object may also be collected.

BRIEF DESCRIPTION OF THE DRAWINGS

The above and other features and advantages of the present invention will become more apparent to those of ordinary skill in the art by describing in detail example embodiments thereof with reference to the attached drawings in which.

DETAILED DESCRIPTION OF THE INVENTION

Figure 1:
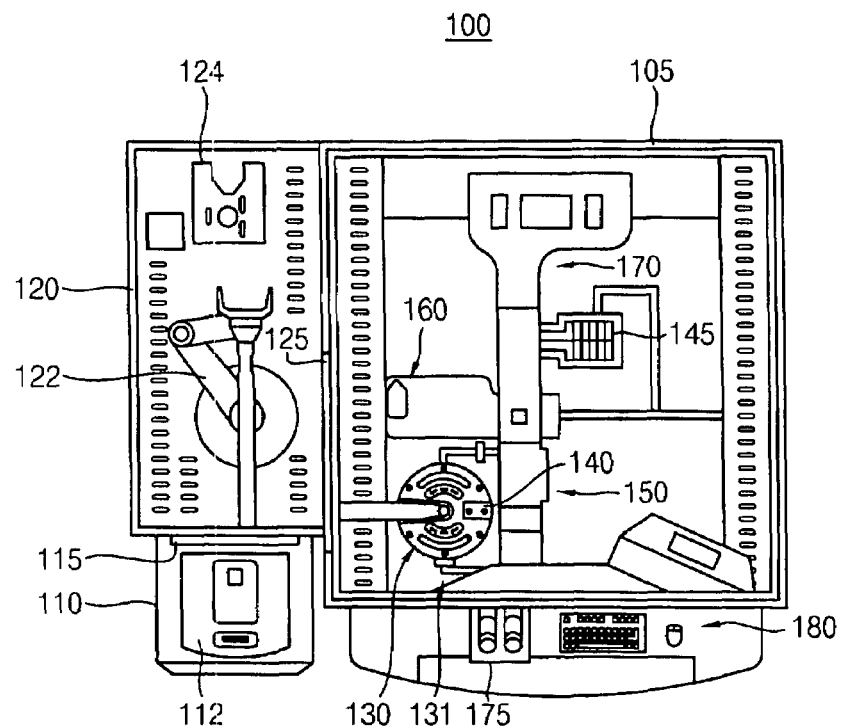
FIG. 1 illustrates an elevated cross-sectional view of an apparatus for examining spectral characteristics of an object in accordance with an example embodiment of the present invention.

Korean Patent Application No. 2006-13083 filed on Feb. 10, 2006, in the Korean Intellectual Property Office, and entitled: "Apparatus and Method for Examining Spectral Characteristics of an Object," is incorporated by reference herein in its entirety.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity. Like reference numerals refer to like elements throughout.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

Figure 2:
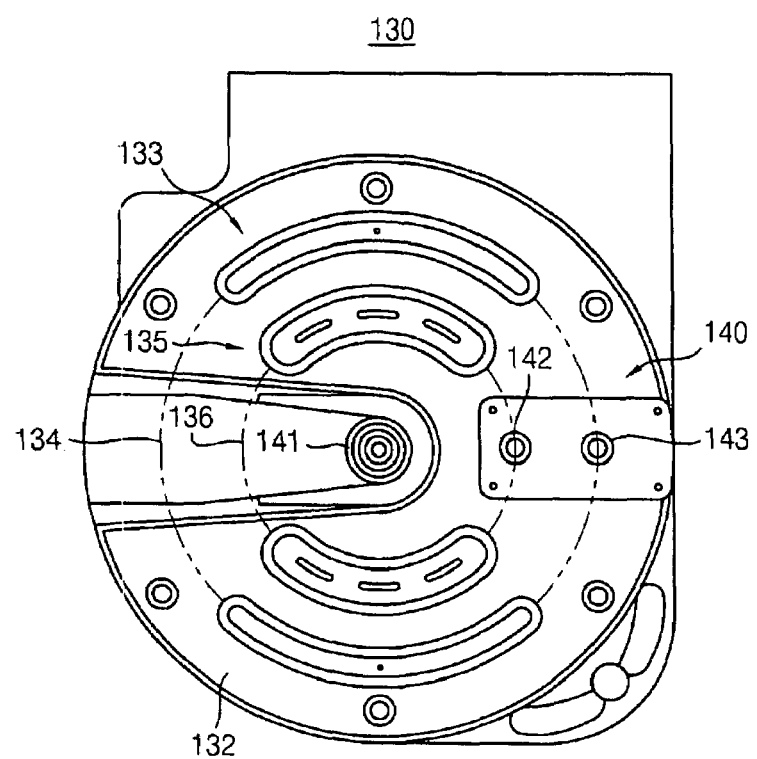
FIG. 2 illustrates an enlarged plan view of a first chuck shown in FIG. 1.
Figure 3:
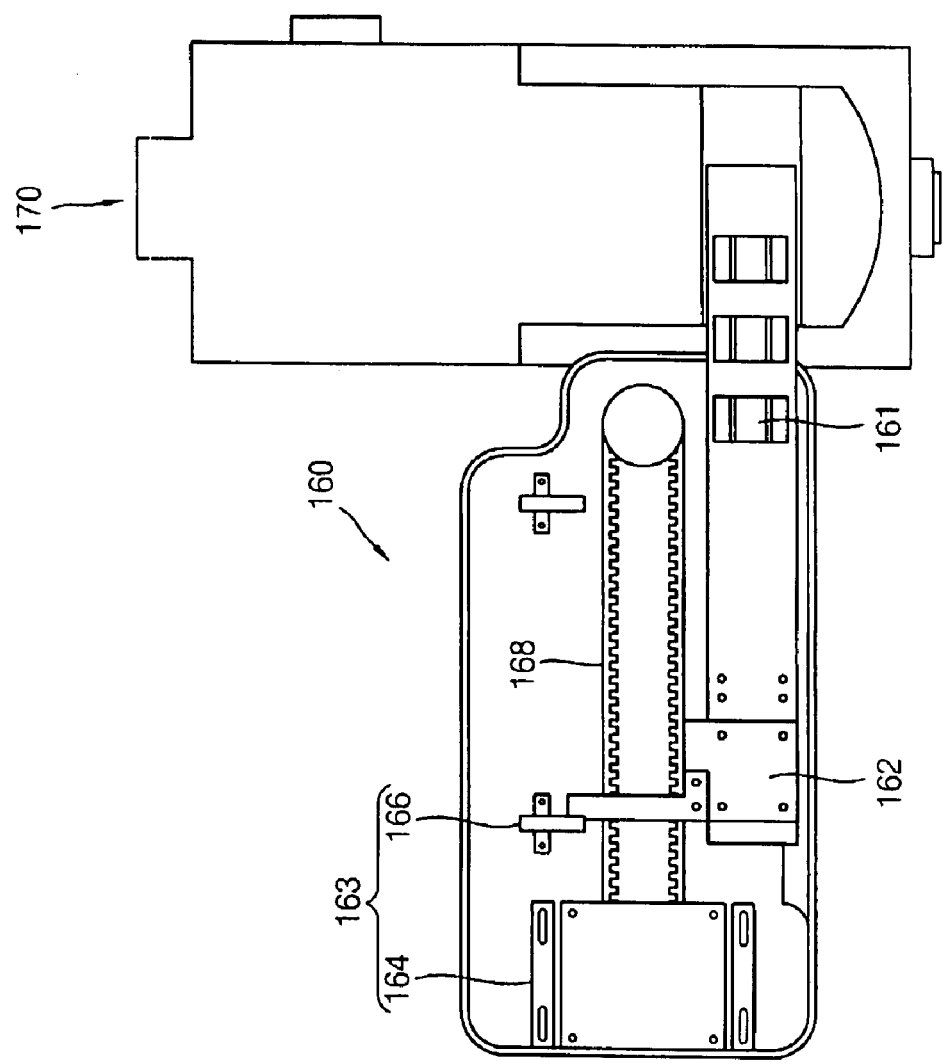
FIG. 3 illustrates an enlarged front view of a standard sample replacement unit shown in FIG. 1.

FIG. 1 illustrates an elevated cross-sectional view of an apparatus for examining spectral characteristics of an object in accordance with an example embodiment of the present invention, FIG. 2 illustrates an enlarged plan view of a first chuck shown in FIG. 1, and FIG. 3 illustrates an enlarged front view of a standard sample replacement unit shown in FIG. 1.

Referring to FIGS. 1 to 3, an apparatus 100 for examining spectral characteristics of an object may include an input/output unit 110, a loading unit 120, a first chuck 130, a first light source assembly 140, a second light source assembly 145, a spectrometer 150, a standard sample replacement unit 160, a spectroscope unit 170, and a control unit 180. The first chuck 130, the first light source assembly 140, the second light source assembly 145, the spectrometer 150, the standard sample replacement unit 160 and the spectroscope unit 170 may be disposed within a housing 105.

The housing 105 may be designed to prevent contaminants from entering, thereby enhancing an accuracy of the examination process. In one embodiment, the inside of the housing 105 is maintained at a clean level that is maintained above class 1. When the clean level inside the housing 105 is above class 1, the environment inside the housing 105 is maintained under a precise atmospheric pressure and may be filtered. The input/output unit 110, the loading unit 120 and the control unit 180 are disposed outside the housing 105, and may serve as the interfaces between a user and the apparatus 100.

The input/output unit 110 and the loading unit 120 enable the user to load or unload a substrate without compromising the clean level conditions inside the housing 105. The input/output unit 110 may be in selective fluid connection with the loading unit 120 through a first shutter 115, and the loading unit 120 may be in selective fluid connection with the housing 105 through a second shutter 125. The input/output unit 110 and the loading unit 120 may be designed so that they may perform their functions in substantially the same manner as those of a normal equipment front-end module (EFEM).

An object to be examined may be provided on a substrate, which, in turn, may be placed into an air-tight container 112, e.g., a front-opening unified pod (FOUP), in preparation for insertion into the input/output unit 110. The substrate may be any size that can reasonably fit into the air-tight container 112, but typically may have a diameter of about 200 mm to 300 mm. The air-tight container 112 with the substrate may be transported inside the housing 105 to the loading unit 120.

The loading unit 120 may include a return robot 122 and a free aligner 124. The return robot 122 may remove the substrate from the air-tight container 112, and may place the substrate on the free aligner 124. After the substrate is aligned on the free aligner 124, the return robot 122 may pass the substrate through the second shutter 125 and load it onto the first chuck 130 inside the housing 105. After the substrate is analyzed, the substrate may be unloaded from the first chuck 130 and may be returned to the input/output unit 110 by reversing the above process.

The input/output unit 110 and the loading unit 120 may be connected to the control unit 180. The control unit 180 may control the input/output unit 110 and the loading unit 120 so that the above-described loading or unloading process may be automatically performed.

The first chuck 130 may include a first chuck plate 132 configured to support the substrate and a first vacuum unit (not shown) that may be disposed under the first chuck plate 132.

The first chuck plate 132 may have a planar, disk shape with a diameter that is substantially the same as or larger than that of the substrate. Unlike the prior art, the chuck plate 132 will accept virtually any substrate that can be processed through the input/output unit 110, and is not limited to a standard substrate size. Thus, an entire bottom surface of the substrate may make contact with a top surface of the first chuck plate 132. The first chuck plate 132 may include a plurality of first vacuum slits 133 and a plurality of second vacuum slits 135 that are in communication with the vacuum unit. The first and second vacuum slits 133 and 135 may have an arcuate shape.

The first and second vacuum slits 133 and 135 may be formed along a plurality of concentric circles in the first chuck plate 132. As illustrated in FIG. 2, each of the first vacuum slits 133 may be formed along a first circumference of a first circle 134, and each of the second vacuum slits 135 may be formed along a second circumference of a second circle 136.

The first circle 134 may have a diameter greater than that of the second circle 136. However, these are not rigid, standard sizes. The first 134 and second circles 136 may be selected for use according to a size of substrates to be examined. For example, when a 200 mm diameter substrate and a 300 mm diameter substrate are examined, the second circle 136 may have a diameter below 200 mm and the first circle may have a diameter between about 200 mm to about 300 mm.

The first vacuum unit may include a vacuum pump (not shown). The first vacuum unit draws in air through the first and second vacuum slits 133 and 135 in the first chuck plate 132, and thereby releasably fixes the substrate to the first chuck plate 132. The first vacuum unit may be in selective communication with the first and second vacuum slits 133 and 135 to accommodate a range of substrates. For example, when a 200 mm substrate is mounted on the first chuck plate 132, the first vacuum unit may communicate with only the second vacuum slit 135, and when a 300 mm substrate is mounted on the first chuck plate 132, the first vacuum unit may communicate with the first vacuum slit 133 and/or the second vacuum slit 135.

The first chuck 130 may be connected to the control unit 180 and controls the actions of the first chuck 130 so that the above-described vacuum attachment process may be performed automatically.

A chuck driving member 131 may be disposed under the first chuck 130, and may be configured to move the first chuck 130 horizontally. The chuck driving member 131 may be located under the second light source unit 145 and the spectroscope unit 170. The chuck driving member 131 may move the first chuck 130 into a position so that a predetermined portion of the substrate mounted on the first chuck 130 is coincident with a central axis of the spectroscope unit 170.

The first light source unit 140 may be integral with the first chuck plate 132, but may be oriented not to interfere with the first and second vacuum slits 133 and 135. The first light source unit 140 may emit light through the pigment layer formed on the substrate so that the transmission value of the pigment may be determined. The first light source assembly 140 may include a first light source 141, a second light source 142 and a third light source 143.

The first, second and third light sources 141, 142 and 143 may be selected to provide a known amount of light in a particular spectrum. For example, when a wavelength band of about 200 to about 400 nm is desired, a deuterium lamp may serve as the light sources 141, 142 and 143. When a wavelength band of about 300 to about 3300 nm is desired, a tungsten halogen lamp or a xenon lamp may serve as the light sources 141, 142 and 143. Additionally, a filament lamp may serve as the light sources 141, 142 and 143.

The light sources 141, 142 and 143 may be arranged from a center of the first chuck plate 132 toward an outside of the first chuck plate 132 so that they are spaced apart from one another. For example, in FIG. 2, the first light source 141 is oriented at the center of the first chuck plate 132, the second light source 142 is oriented within a radius of about 100 mm from the center, and the third light source 143 is oriented within a radius of about 100 to about 150 mm from the center.

The light sources 141, 142 and 143 may illuminate the bottom surface of the substrate mounted on the first chuck plate 132. The light sources 141, 142 and 143 may be connected to the control unit 180 to be selectively operated. For example, when a 200 mm substrate is mounted on the first chuck plate 132, the first and second light sources 141 and 142 may be operated, and when a 300 mm substrate is mounted on the first chuck plate 132, all of the first, second and third light sources 141, 142 and 143 may be operated. Light transmitted by the substrate may be collected by the spectroscope unit 170.

The substrate may include a transparent plate on which at least one pigment layer is formed or deposited. The transparent plate may include a glass plate or an acrylic plate. The pigment layer is formed on the transparent plate to a thickness of several micrometers. Additionally, the pigment layer may be patterned. That is, the substrate may include a color filter, or alternatively, the substrate may include a transparent plate on which a photoresist film is formed to a predetermined thickness.

Some of the light emitted onto the substrate will pass through the pigment layer formed on the substrate. The pigment layer may absorb ultraviolet or visible light having a predetermined wavelength, depending on the type of pigment. When the wavelength of the absorbed light is determined, the molecular composition, molecular concentration and thickness of the pigment layer may be evaluated. The wavelength of the absorbed light may be determined by analyzing the light transmitted by the substrate having the pigment layer thereon. The light absorption value of the pigment layer may be determined from the light transmission value of the pigment layer.

The above-mentioned light absorption process may be performed over an entire surface of the substrate, so that a maximum amount of light may illuminate the substrate. That is, when all the light sources 141, 142 and 143 are operating, the light absorption analysis process may be performed more accurately. As a result, the first light source assembly 140 may include at least three light sources 141, 142, 143, as illustrated in FIG. 2.

Generally, in order to maximize accuracy, the substrate should be relatively large, e.g., have a diameter of about 300 mm. The substrate may be mounted on the chuck plate which is large enough to fully support the substrate and to prevent the substrate from warping. Thus, the entire substrate, i.e., the entire bottom surface of the substrate, may make contact with the chuck plate 132. This is not possible with conventional devices. Some of the light emitted from a light source of a conventional device may not pass through the substrate because the conventional chuck plate itself blocks some of the light. However, in accordance with example embodiments of the present apparatus 100, the light emitted from the first light source assembly 140 may illuminate and be transmitted by the substrate even when the entire bottom surface of the substrate makes contact with the first chuck plate 132. That is, the light transmission value of a substrate having a relatively large diameter may be determined in the apparatus 100. This may be achieved by incorporating the light sources 141, 142, 143 into the chuck plate 132, thereby maximizing illumination of the substrate.

Referring again to FIG. 1, the spectroscope unit 170 may be disposed at a center of the housing 105. The second light source assembly 145 may be adjacent to the spectroscope unit 170, and light from the second light source assembly 145 may illuminate a top surface of the substrate at a predetermined location by passing through the spectroscope unit 170. The second light source assembly 145 may include a plurality of light sources (not shown), similar to the plurality of light sources 141, 142, 143 in the first light source assembly 140.

Light reflected from the substrate after illumination by the second light source assembly 145 may be collected by the spectroscope unit 170. Thus, the spectroscope unit 170 may provide the spectrometer 150 with light transmitted by and/or reflected from the substrate.

The second light source assembly 145 and the first light source assembly 140 may both be directed by the control unit 180 at substantially the same time. Thus, the light transmission value and the light reflection value of the pigment layer may be simultaneously analyzed and determined.

The spectroscope unit 170 may include a microscope. An objective lens assembly (not shown) may be oriented adjacent to the upper surface of the substrate, and an ocular lens assembly or viewfinder 175 may be outside of the housing 105. The microscope provides an enlarged image of the predetermined location on the substrate that may be used by the spectroscope unit 170, thereby confirming whether or not the light is exactly incident on the predetermined location. Additionally, the spectroscope unit 170 may include a diffraction grid configured to control the bandwidth of the collected light, and a concave lens, a focus control member, and a slit width control member. The standard sample replacement unit 160 may be oriented adjacent to the spectroscope unit 170.

The standard sample replacement unit 160 may include a slider 162 and a slider driving member 163. A plurality of standard samples 161 may be mounted on the slider 162, and the slider driving member 163 may move the slider 162 to the inside of the spectroscope unit 170.

Referring to FIG. 3, a standard sample 161 may include known, standard spectral qualities to be used to confirm the proper functioning of the apparatus 100. The proper functioning of the apparatus 100 may be determined through observing and deriving the spectral characteristics of the standard sample 161 via a standardized predetermined method.

A plurality of standard samples 161 may be prepared to provide a variety of spectral types or pigment characteristics. The standard samples 161 may be regularly arranged on the slider 162 for selective, controlled insertion into the spectroscope unit 170.

The slider driving member 163 may include a step motor 164, a sensor 166 and a belt 168. The slider 162 may be connected to the belt 168. The step motor 164 may rotate the belt 168, and the slider 162 connected to the belt 168 may be moved into the spectroscope unit 170.

The sensor 166 may confirm the location of the slider 162 by detecting the amount of rotation of the belt 168. Thus, the sensor 166 may indirectly confirm the location of the slider 162. The confirmation of the location of the slider 162 may be used to ensure that the desired standard sample 161 is oriented to properly provide light to the spectroscope unit 170. The sensor 166 may provide information about the rotation or movement of the belt 168 for the control unit 180. The control unit 180 may control the step motor 164 according to information from the sensor 166 so that the desired standard sample 161 may be properly oriented in the spectroscope unit 170.

Light may illuminate the standard sample 161 in substantially the same manner as for the substrate above, so that a light transmission value and a light reflection value for the standard sample 161 may be determined.

The results of the spectral examination may be provided to the control unit 180, which compares the result of the spectral examination with the known values for the standard sample 161 to determine whether the apparatus 100 is functioning properly.

The above-mentioned process for confirming the proper functioning of the apparatus 100 may be performed when desired. When the standard sample replacement unit 160 is inside the housing 105, the housing 105 does not even need to be opened. Thus, the clean level inside the housing 105 may be uncompromised.

The spectrometer 150 may be connected to the spectroscope unit 170, and may receive the light transmitted through the substrate or reflected from the substrate via the spectroscope unit 170. The spectrometer 150 may analyze the received light, and may separate the analyzed light according to wavelength. The spectrometer 150 may divide polychromatic light into monochromatic light using an incident slit, a dispersion member, an emission slit, or other available means. The incident slit, a dispersion member, an emission slit, or other means may be integral with the spectroscope unit 170.

Spectral data determined in the spectrometer 150 may be provided to the control unit 180 for display in a display member of the control unit 180. Additionally or alternatively, the spectral data may be stored in a storage member of the control unit 180.

Hereinafter, a method for examining spectral characteristics of an object using the apparatus 100 shown in FIG. 1 is illustrated.

The air-tight container 112 containing the substrate may be moved into the input/output unit 110. The substrate may be removed from the air-tight container 112 using the return robot 122. The substrate may then be mounted on the free aligner 124.

The free aligner 124 may align the substrate, and may simultaneously determine a size of the substrate mounted on the free aligner 124. The size of the substrate may be determined using the free aligner 124, or alternatively, the size of the substrate may be determined when the substrate is removed from the air-tight container 112.

The substrate, which is temporarily stored within reach of the return robot 122, may be removed from the free aligner 124 to be loaded onto the first chuck 130.

When the substrate is loaded onto the first chuck 130, the first vacuum unit may be operated to releasably fix the substrate to the first chuck plate 132. The first and second vacuum slits 133 and 135 may be selectively in communication with the first vacuum unit in order to hold the substrate in place on the chuck plate 132. For example, when the substrate has a diameter of about 200 mm, the second vacuum slit 135 may be in communication with the first vacuum unit, whereas the first vacuum slit 133 may not be in communication with the first vacuum unit. When the substrate has a diameter of about 300 mm, both the first and second vacuum slits 133 and 135 may be in communication with the first vacuum unit. That is, the substrate may be stably and releasably fixed to the first chuck plate 132 regardless of the size of the substrate. Full support of the substrate by the chuck plate 132 may prevent or reduce distortion of the substrate.

The first chuck 130, onto which the substrate is fixed, may be horizontally moved under the spectroscope unit 170.

The first light source assembly 140 may illuminate the bottom surface of the substrate. Illumination of a predetermined location on the substrate by the first light source assembly 140 may be confirmed using the spectroscope unit 170 and/or the microscope.

The spectra of the light emitted from the first light source unit 140 may be selected according to types or characteristics of the pigment layer formed on the substrate. Illuminated spots may be spaced apart from one another from a center of the first chuck 130 toward an outside of the first chuck 130 in order to examine the spectral characteristics of the entire substrate. The light transmission value of the pigment layer may be detected more accurately when the entire substrate is examined.

The light transmitted through the substrate may be collected by the spectroscope unit 170. The collected light is polychromatic light. The polychromatic light may be divided into a number of monochromatic light samples, e.g., using the diffraction grid in the spectroscope unit 170. The bandwidth of the monochromatic light may be controlled, e.g., using a concave lens, a focus control member, a slit width control member, and other means.

As illustrated above, the light transmission value of the pigment layer may be determined by illuminating the bottom surface of the substrate, and simultaneously, the light reflection value of the pigment layer may be determined by illuminating the upper surface of the substrate. The light reflection value of the pigment layer may be detected by using the second light source assembly 145 which is adjacent to the spectroscope unit 170. The light reflecting from the upper surface of the substrate may also be collected by the spectroscope unit 170, and the collected light may be divided in the spectrometer 150 according to wavelength. Thus, the light reflection value of the pigment layer may be determined.

The various types, characteristics or states of the pigment may be presented with a data display in the control unit 180. A predetermined location on the substrate may be oriented to be coincident with the axis of light of the spectroscope unit 170 using the chuck driving member 131 so that the light transmission value and the light reflection value may be detected for the entire substrate.

Figure 4:
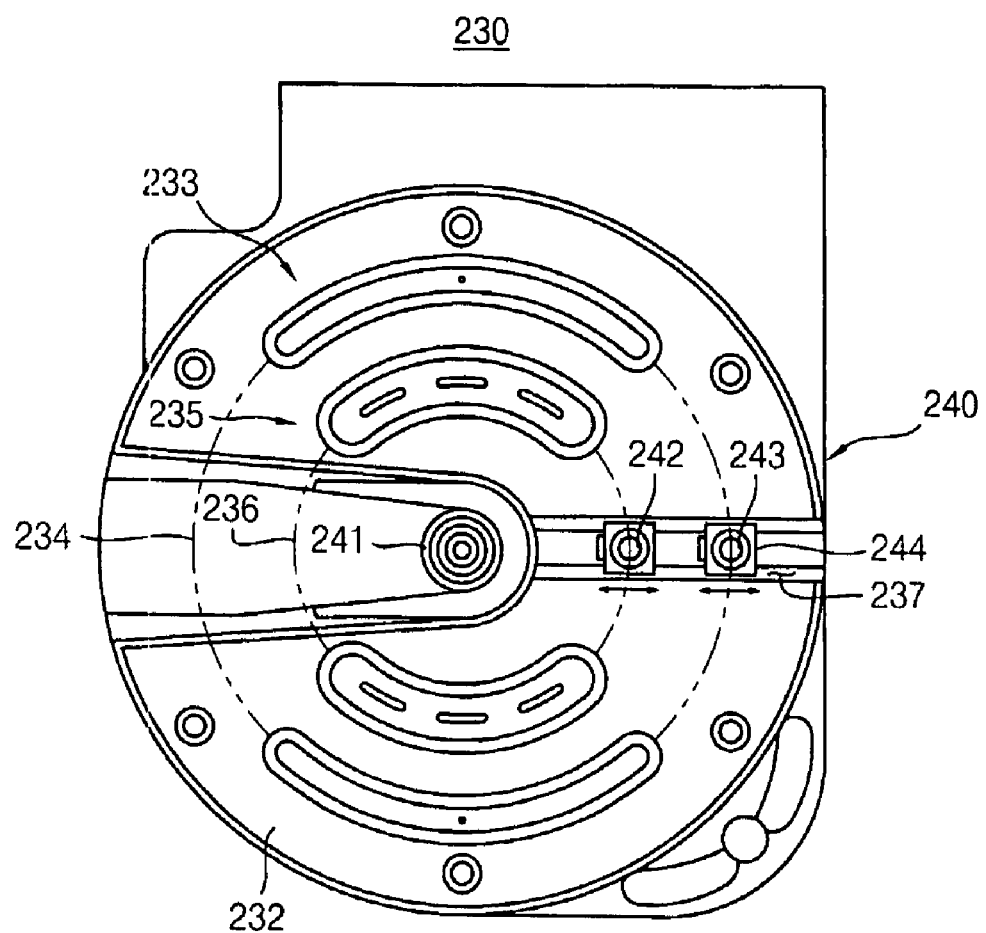
FIG. 4 illustrates an enlarged plan view of a second chuck in accordance with an example embodiment of the present invention.

FIG. 4 illustrates an enlarged plan view of a second chuck in accordance with an embodiment of the present invention.

The apparatus 100 for examining the spectral characteristics of an object may include the second chuck 230 in place of the first chuck 130. The apparatus in this embodiment may be substantially the same as the apparatus 100 described in FIG. 1 except for the second chuck 230. Thus, a detailed explanation will be omitted hereinafter except regarding the second chuck 230.

The second chuck 230 may include a second chuck plate 232 configured to support the substrate and a second vacuum unit (not shown) oriented under the second chuck plate 232. The second chuck plate 232 may have a disk shape whose diameter is substantially the same as or larger than that of a substrate. Thus, an entire bottom surface of the substrate may make contact with a top surface of the second chuck plate 232. The second chuck plate 232 may have a plurality of third vacuum slits 233 and a plurality of fourth vacuum slits 235 therein. Each of the third and fourth vacuum slits 233 and 235 may have an arcuate shape. The third and fourth vacuum slits 233, 235 may correspond to the first and second vacuum slits 133, 135 in the first chuck 130.

The third and fourth vacuum slits 233 and 235 may be formed along a plurality of concentric circles in the second chuck plate 232. Each of the third vacuum slits 233 may be formed along a circumference of a third circle 234, and each of the fourth vacuum slits 235 may be formed along a circumference of a fourth circle 236.

The third circle 234 may have a diameter greater than that of the fourth circle 236. The third and fourth vacuum slits 233 and 235 may be in communication with the second vacuum unit.

The second vacuum unit may draw air in over the second chuck plate 232 and through the third and fourth vacuum slits 233 and 235, so that the substrate may be releasably fixed to the second chuck plate 232. The second vacuum unit may be in selective communication with the third and fourth vacuum slits 233 and 235.

A light slit 237 in the second chuck plate 232 may extend radially from the center of the second chuck plate 232 toward the outside of the second chuck plate 232. The light slit 237 may be oriented so as not to interfere with the third and fourth vacuum slits 233 and 235. The light slit 237 may have a linear shape. Alternatively, a plurality of arcuate light slits 237 may be formed along concentric circles 234 and 236 in the second chuck plate 232.

The third light source assembly 240 may be integral with the second chuck plate 232. The third light source assembly 240 may provide light to determine the transmission value of a pigment layer formed on the substrate. The third light source unit 240 may include a fourth light source 241, a fifth light source 242 and a sixth light source 243. The fourth, fifth and sixth light sources 241, 242 and 243 may correspond to the first, second and third light sources 131, 132 and 133 of the first chuck 130. The fourth, fifth and sixth light sources 241, 242 and 243 may be selected according to a desired wavelength. For example, a tungsten halogen lamp, a xenon lamp or a filament lamp may serve as the light sources 241, 242 and 243, depending upon the desired spectral characteristics.

The fourth light source 241 may be oriented at the center of the second chuck plate 232, and the fifth and sixth light sources 242 and 243 may be disposed within the light slit 237. Alternatively, each of the fourth, fifth and sixth light sources 241, 242 and 243 may be disposed within the light slit 237. When the plurality of arcuate light slits 237 is included in the second chuck plate 232, the fifth and sixth light sources 242 and 243 may be disposed within separate light slits. The fifth and sixth light sources may be provided on additional mounts 244 to facilitate movement within light slit 237.

A light source driving member (not shown) may be disposed under the fifth and sixth light sources 242 and 243 formed within the light slit 237. The light source driving member may move the fifth and sixth light sources 242 and 243 along the light slit 237.

Locations of the fifth and sixth light sources 242 and 243 may be changed. For example, the fifth light source 242 may be oriented within a radius of about 100 mm from the center of the second chuck plate 232, and the sixth light source 243 may be oriented within a radius of about 100 mm to about 150 mm from the center of the second chuck plate 232. When a substrate having a diameter of about 300 mm is mounted on the second chuck plate 232, the fifth light source 242 may be located at a radius of about 100 mm from the center of the second chuck plate 232, and the sixth light source 243 may be located at a radius of about 150 mm from the center of the second chuck plate 232.

The light sources 241, 242 and 243 may illuminate a bottom surface of the substrate mounted on the second chuck plate 232. The light sources 241 and 242 and 243 may be connected to the control unit 180 (see FIG. 2) to be selectively operated. For example, when a 200 mm substrate is mounted on the second chuck plate 232, the fourth and fifth light sources 241 and 242 may be operated, and when a 300 mm substrate is mounted on the second chuck plate 232, the fourth, fifth and sixth light sources 241, 242 and 243 may be operated. Alternatively, the fifth and sixth light source 242, 243 may be adjusted within the light slit 237 by the driving member, and may be controlled by the controller 180, to provide maximum illumination on even a small substrate.

The process for determining the light absorption value of a substrate is most accurate when it is performed over the entire surface of the substrate, and a maximum amount of light is emitted onto the substrate. That is, when more individual light sources, such as 241, 242 and 243, are available and used, the absorption value determination process is performed more accurately. However, the number of light sources attached to the chuck 230 is limited.

According to some embodiments of the present invention, the light transmission value for the entire surface of the substrate may be determined by changing the locations of the light sources 241, 242 and 243. That is, the light transmission value for the entire surface of the substrate may be efficiently detected even without increasing the number of light sources 241, 242 and 243.

According to the present invention, substrates having various sizes may be stably and releasably fixed to a chuck so that an entire surface of the substrate may make contact with the chuck. Thus, warping of the substrate may be prevented or reduced. The substrate may be easily released from the chuck by removing the vacuum. Additionally, the light transmission value and a light reflection value of the substrate may be determined regardless of the size of the substrate. That is, the examination and determination of the spectral characteristics of a pigment layer formed on the substrate may be performed efficiently and automatically, thereby enabling the creation of a color filter with excellent qualities.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures.

Therefore, it is to be understood that the foregoing is illustrative of the present invention and is not to be construed as limited to the specific example embodiments disclosed, and that modifications to the disclosed example embodiments, as well as other example embodiments, are intended to be included within the scope of the appended claims. The present invention is defined by the following claims, with equivalents of the claims to be included therein.

What is claimed is:

1. An apparatus for examining spectral characteristics of transmitted light through an object, the apparatus comprising:
   a chuck including a chuck plate configured to support and releasably fix the object, wherein the chuck is larger than the object;
   a first light source assembly integral with the chuck and configured to illuminate a bottom surface of the object with light having a predetermined spectrum and intensity; and
   a transmission analysis unit for collecting and analyzing light transmitted through the object,
   wherein the chuck plate includes a light slit extending radially from the center of the chuck plate toward an outside of the chuck plate, and
   wherein the first light source assembly includes:
      a light source formed within the light slit; and
      a light source driving member for translating the light source along the light slit.

2. The apparatus as claimed in claim 1, wherein the first light source assembly comprises a plurality of light sources that are spaced apart from one another from a center of the chuck toward an outside of the chuck.

3. The apparatus as claimed in claim 2, wherein the plurality of light sources are arranged along a straight line.

4. The apparatus as claimed in claim 1, wherein the first light source assembly comprises:
   a first light source formed at the center of the chuck;
   a second light source formed within a radius of about 100 mm from the center of the chuck; and
   a third light source formed within a radius of about 100 mm to about 150 mm from the center of the chuck.

5. The apparatus as claimed in claim 1, further comprising a second light source assembly oriented over the chuck to illuminate a top surface of the object; and
   a reflection analysis unit for collecting reflected light and for analyzing light reflected by the object.

6. The apparatus as claimed in claim 1, further comprising a chuck driving member below the chuck to move the chuck horizontally.

7. The apparatus as claimed in claim 1, wherein the chuck comprises:
   the chuck plate having a plurality of vacuum slits formed along a plurality of concentric circles in the chuck plate, wherein the vacuum slits do not overlay the first light source assembly; and
   a vacuum unit in communication with the vacuum slits to draw in air through the vacuum slits to releasably fix the object onto the chuck plate.

8. The apparatus as claimed in claim 7, wherein the chuck plate comprises a horizontal area that is substantially the same as or greater than that of the object.

9. The apparatus as claimed in claim 7, wherein the chuck plate comprises:
   a first vacuum slit formed within a radius of about 100 mm from a center of the chuck plate; and
   a second vacuum slit formed within a radius of about 100 to about 150 mm from the center of the chuck plate.

10. The apparatus as claimed in claim 9, wherein the first light source assembly comprises:
   a first light source formed at the center of the chuck plate;
   a second light source formed at substantially the same distance from the center of the chuck plate as the first vacuum slit; and
   a third light source formed at substantially the same distance from the center of the chuck plate as the second vacuum slit.

11. The apparatus as claimed in claim 1, wherein the first light source assembly comprises a plurality of light sources and light source driving members.

12. The apparatus as claimed in claim 1, further comprising:
   a slider mechanism configured to support standard samples; and
   a slider driving member configured to move the slider inside the transmission analysis unit.

13. The apparatus as claimed in claim 12, further comprising a plurality of standard samples.

14. The apparatus as claimed in claim 1, further comprising an interface for receiving a loading unit for automatically loading the object onto the chuck.

15. The apparatus as claimed in claim 1, further comprising a housing configured to contain the chuck, the first light source assembly and the transmission analysis unit to protect the chuck, the first light source assembly, and the transmission analysis unit from contaminants.

16. The apparatus as claimed in claim 2, wherein at least one of the plurality of light sources is capable of being moved radially from the center of the chuck.

17. A method for examining spectral characteristics of transmitted light through an object, the method comprising:
   mounting the object onto a chuck including a chuck plate having a size larger than that of the object, wherein the chuck plate includes a light slit extending radially from the center of the chuck plate toward an outside of the chuck plate;
   illuminating a bottom surface of the object from a light source assembly integral with the chuck, wherein the light source assembly includes a light source formed within the light slit;
   collecting light transmitted by the object; and
   deriving a light transmission value for the object,
   wherein illuminating the bottom surface of the object includes driving a light source driving member to translate the light source along the light slit.

18. The method as claimed in claim 17, wherein the light source assembly comprises a plurality of light sources integral with the chuck that are spaced apart.

19. The method as claimed in claim 17, further comprising:
   illuminating a top surface of the object; and
   deriving a light reflection value for the object.

* * * * *